United States Patent [19]

Bailey et al.

[11] Patent Number: 4,801,761
[45] Date of Patent: Jan. 31, 1989

[54] PERFLUORO-1,1-DI(ORTHOXYLYL)ALKYL COMPOUNDS

[75] Inventors: Webb I. Bailey, Fogelsville; John T. Lileck, Tamaqua, both of Pa.

[73] Assignee: Air Products and Chemicals, Inc., Allentown, Pa.

[21] Appl. No.: 17,390

[22] Filed: Feb. 20, 1987

[51] Int. Cl.$^4$ ............................................. C07C 23/18
[52] U.S. Cl. ..................................... 570/130; 228/42; 228/218
[58] Field of Search ........................................ 570/130

[56] References Cited

U.S. PATENT DOCUMENTS

| | | |
|---|---|---|
| Re. 30,399 | 9/1980 | Ammann . |
| 2,459,780 | 1/1949 | McBoe . |
| 2,653,912 | 9/1953 | Ross . |
| 3,440,277 | 4/1969 | Holland . |
| 4,173,573 | 11/1979 | Schulz . |
| 4,549,686 | 10/1985 | Sargent . |

OTHER PUBLICATIONS

Aikman et al, J. Org. Chem., 1982, 47, 2790-2792.
Bellany et al, CA 48, 11192c (1954), Nature, 173, 633-634 (1954).
Barbour et al, CA 47, 1624g, J. Applied Chem. (London), 2, 127-133 (1952).
47-11748 (11,748), Japanese Authors: Kato & Shibuya, Title: Method for Producing 1,1-diarylethe, Date: Apr. 12, 1972, Filed: Nov. 13, 1968.
127-33 (Chemical Abstracts), vol. 47, #1624, A-H, Barbour et al.

*Primary Examiner*—Howard T. Mars
*Attorney, Agent, or Firm*—Geoffrey L. Chase; James C. Simmons; William F. Marsh

[57] ABSTRACT

Novel compositions of matter are disclosed; perfluoro-1,1-di(orthoxylyl) methane, perfluoro-1,1-di(orthoxylyl) ethane and perfluoro-1,1-di(orthoxylyl) propane. The compositions are made by cobalt trifluoride fluorination of 1,1-di(orthoxylyl) methane, 1,1-di(orthoxylyl) ethane and 1,1-di(orthoxylyl) propane. The compositions have utility as vapor phase soldering fluids.

4 Claims, No Drawings

PERFLUORO-1,1-DI(ORTHOXYLYL)ALKYL COMPOUNDS

TECHNICAL FIELD

The present invention is directed to novel compositions comprising perfluoro-1,1-di(orthoxylyl) methane which is produced by fluorinating 1,1-di(orthoxylyl) methane or 1,1-di(orthoxylyl) ethane; perfluoro-1,1-di(orthoxylyl) ethane which is produced by fluorinating 1,1-di(orthoxylyl) ethane and perfluoro-1,1-di(orthoxylyl) propane which is produced by fluorinating 1,1-di(orthoxylyl) propane; all such fluorinations are conducted with cobalt trifluoride which fully fluorinates all hydrogen sites on the molecules. More specifically, the present invention is directed to perfluoro-1,1-di(orthoxylyl) methane, perfluoro-1,1-di(orthoxylyl) ethane and perfluoro-1,1-di(orthoxylyl) propane having utility as high temperature vapor phase soldering fluids which are heat stable, inert and do not release any significant amount of perfluoroisobutylene under sustained high temperature utilization.

BACKGROUND OF THE PRIOR ART

Various prior art compounds have been synthesized and more specifically fluorinated to provide at least partially fluorinated organic compounds having high degrees of heat stability. For instance, in U.S. Pat. No. 2,653,912, compounds are disclosed which are not substituted on the same or adjacent carbon atoms with hydrogen and fluorine. Such compounds include alpha(x trifluoromethylphenyl)beta(y trifluoromethylphenyl)tetrafluoroethane and similar compounds at column 2 of the patent. The compounds are synthesized by the dimerization of a monoaryl compound to produce the multiple aryl compounds of the patent. The compounds are useful as dielectric compositions, plasticizers for resins, heat transfer agents, hydraulic fluids and similar uses where elevated temperature stability and avoidance of chemical deterioration are necessary. The patent teaches that optimum stability is derived when the composition is hydrogenated at low pressure to remove unsaturated linkages.

U.S. Pat. No. 3,440,277 discloses various substituted fluorinated biphenyl compounds, particularly those substituted in the 3,3',4,4' positions. The compounds typically have radicals attached to the aromatic ring comprising carboxyl, bromine or hydrogen. The compounds have good heat stability and stability in the presence of oxygen and can be utilized as intermediates in the preparation of polymeric resins and oils.

Compound aromatic ring compounds are also known to be fluorinated as in U.S. Pat. No. 2,459,780 wherein various compounds, including perfluoroperhydrophenanthrene, are indicated as having utility as high temperature heat transfer media because of their non-flammability and stability to heat and oxidation.

The use of such fluorocarbon materials for vapor phase soldering is disclosed in RE No. 30,399 which describes the soldering of electronic components in the vapor of a boiling liquid comprising a fluorocarbon. The patent teaches that various FREON ® compounds are useful as vapor phase soldering fluids.

U.S. Pat. No. 4,173,573 discloses a method for condensing orthoxylene with acetaldehyde to produce 1,1-bis(3,4-dimethylphenyl) ethane.

U.S. Pat. No. 4,549,686 discloses that perfluoroperhydrophenanthrene is a viable composition for utilization in vapor phase soldering wherein the compound has a boiling point of approximately 215° C. and is useful on solders having a tin-lead composition wherein the tin content is in the range of 55-80%, the remainder comprising lead.

Japanese Published Patent Application No. 72 11,748 of Apr. 12, 1972 Kato, et al. assigned to Asahi Chemical Industry Co. Ltd. discloses the production of 1,1-diarylethanes from m-xylene and formaldehyde or paraacetaldehyde using an acid catalyst.

A. K. Barbour, et al. in Journal of Applied Chemistry Vol. 2, pp. 127–133 (1952) disclosed the cobalt trifluoride fluorination of various diaryl compounds to produce room temperature, solid fluorinated compounds, including $(C_6F_{11}CF_2CF_2)_2CF_2$ and $(C_6F_{11}CF_2CF_2CF_2)_2$.

BRIEF SUMMARY OF THE INVENTION

The present invention comprises novel compositions of matter consisting of perfluoro-1,1-di(orthoxylyl) alkyl compounds having the structural formula of:

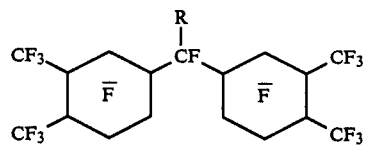

wherein $\overline{F}$ indicates that all available sites are fluorinated and there are no carbon to carbon double bonds and R is selected from the group consisting of F, $CF_3$ and $C_2F_5$. The compounds are made by the fluorination of 1,1-di(orthoxylyl) methane, 1,1-di(orthoxylyl) ethane or 1,1-di(orthoxylyl) propane respectively in the vapor state in the presence of cobalt trifluoride at a temperature of 230–415° C. The compounds are useful in a process of vapor phase soldering wherein a component to be soldered is immersed in a vapor bath to melt the solder and the component is then withdrawn from the vapor bath wherein the improvement for soldering at temperatures up to approximately 290° C. comprises that the vapor bath is selected from the group consisting of perfluoro-1,1-di(orthoxylyl) methane, perfluoro-1,1-di(orthoxylyl) ethane, perfluoro-1,1-di(orthoxylyl) propane and mixtures thereof.

DETAILED DESCRIPTION OF THE INVENTION

The present invention comprises novel compositions of matter, namely; perfluoro-1,1-di(orthoxylyl) alkyl compounds which has the following structural formula:

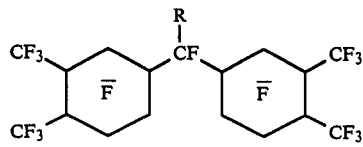

wherein $\overline{F}$ indicates that all available sites are fluorinated and that there are no carbon to carbon double bonds and R is selected from the group consisting of F, $CF_3$ and $C_2F_5$. The methylene bridged compound has an empirical formula of $C_{17}F_{32}$, a predicted boiling point of approximately 250° C. and an actual boiling point range of 250° to approximately 260° C. The ethane bridged compound has an empirical formula of $C_{18}F_{34}$, a predicted boiling point of approximately 270° C. and an actual boiling point range of approximately 250° to 260° C. based upon the carryover effect resulting from a distillation of limited efficiency. The propane bridged compound has an empirical formula of $C_{19}F_{36}$ and a predicted boiling point of approximately 290° C. These compounds have a utility as high boiling inert fluids, and more specifically as vapor phase soldering fluids used in reflowing solder in a process for soldering small electronic components to one another or to a printed circuit board or other substrate.

The methylene bridged compound has a molecular weight of 812, the ethane bridged compound has a molecular weight of 862 and the propane bridged compound has a molecular weight of 912. The compounds are electrically nonconducting and the vapors produced by boiling the compositions are nonoxidizing, chemically stable and inert, as well as being nontoxic and producing no toxic by-products. Additionally, the compounds have been shown to leave no residues on components which are subjected to the vapor of the compositions after the component has been removed from such vapors. The compounds are fully fluorine saturated and can also be named perfluoro,perhydro-1,1-di(orthoxylyl) methane, ethane or propane.

A unique advantage of perfluoro-1,1-di(orthoxylyl) methane, ethane or propane is that they are liquid at room temperature. Compounds having carbon numbers in the range of $C_{17}$ to $C_{19}$, such as the compositions of the present invention, are usually solid at room temperature. This affords a unique advantage for their utility as a high temperature soldering fluids because users desire a working fluid that can be easily loaded in soldering machinery and that will not salt-out or solidify on machinery, cooling coils or components that have been soldered. It has also been found that these compounds exhibited unusual stability during formulation and as the fluorinated products.

The basic hydrocarbon starting materials are, 1,1-di(orthoxylyl) ethane (CAS# [1742-14-9]), which is produced by condensing ortho-xylene with acetaldehyde in contact with an acid catalyst to obtain 1,1-di(orthoxylyl) ethane; the 1,1-di(orthoxylyl) methane (CAS# [726-05-6]) homolog which can be made by condensing ortho-xylene with formaldehyde in contact with an acid catalyst and 1,1-di(orthoxylyl) propane, which is produced by condensing ortho-xylene with propionaldehyde in contact with an acid catalyst. The acid catalyst include sulfuric acid, hydrofluoric acid and p-toluenesulfonic acid. Such synthetic routes are described further in U.S. Pat. No. 4,173,573 hereby incorporated herein by reference.

The perfluoro-1,1-di(orthoxylyl) alkyl compound is preferably produced in a direct fluorination with cobalt trifluoride. Exemplary of this production technique is the following example.

EXAMPLE 1

In a typical reaction, 1,1-di(orthoxylyl) ethane is vaporized into a cobalt trifluoride reactor operating at 230° to 350° C. The resulting fluorochemical product, containing perfluoro-1,1-di(orthoxylyl) methane is collected and separated from hydrogen fluoride by-products. The fluorochemical is purified by distillation to give a product that is liquid at room temperature and has a boiling point range of approximately 250°-260° C. The fluorination process predominantly cleaves the methyl group from the bridging chain between the two ring constituents to change the ethyl bridge to a methylene bridge, but a mixture of the ethyl and methylene bridged compounds are produced which are separated by distillation. Milder fluorination conditions increases the amount of ethyl bridged compound.

EXAMPLE 2

77 g of 1,1-di(orthoxylyl) ethane was heated to its boiling point in a vaporizer while purging with nitrogen gas. The 1,1-di(orthoxylyl) ethane/nitrogen gas stream was fed to a heated reactor 6" in diameter and 4' long containing approximately 35 lbs of cobalt trifluoride. The reactor was held at approximately 345° C. in the first half of the reactor and approximately 415° C. in the last half of the reactor. The 1,1-di(orthoxylyl) ethane feed was subsequently converted to 162 g of a perfluorochemical. The crude fluorochemical was filtered to remove any solids and passed thru alumina to remove any active fluorides.

EXAMPLE 3

143 g of 1,1-di(orthoxylyl) ethane was heated to its boiling point in a vaporizer while purging wih nitrogen gas. The 1,1-di(orthoxylyl) ethane/nitrogen gas stream was fed to a heated reactor 6" in diameter and 4' long containing approximately 35 lbs of cobalt trifluoride. The reactor was held at approximately 345° C. in the first half of the reactor and approximately 415° C. in the last half of the reactor. The 1,1-di(orthoxylyl) ethane feed was subsequently converted to 201 g of a perfluorochemical. The crude fluorochemical was filtered to remove any solids and passed thru alumina to remove any active fluorides.

EXAMPLE 4

215 g of a crude perfluorochemical prepared in a similar manner to Examples 2 and 3 above was distilled through a glass packed column. A product was collected which had a boiling range of 240°-270° C. which represented 60.5% of the original charge. Analysis by $^{19}F$ NMR spectroscopy and GC/MS (gas chromatography/mass spectroscopy) confirmed the presence of perfluoro-1,1-di(orthoxylyl) methane. This analytical data is summarized in Table 1.

TABLE 1

| $^a$NMR-$^{19}$F | | | |
|---|---|---|---|
| | $CF_3$ $-63$ to $-73^b$ multiplet | $CF_2$ $-98$ to $-140^b$ multiplet | $CF$ $-161$ to $-189^b$ multiplet |
| Relative F atomic ratio | | | |
| calculated | 2.0 | 2.3 | 1.0 |
| observed | 1.6 | 1.9 | 1.0 |
| $^c$MASS SPECTRUM (m/e) | | | |
| calculated | | | 812 ($C_{17}F_{32}$) |
| observed | | | 812 ($C_{17}F_{32}$) |

$^a$in $CFCl_3$
$^b$ppm from $CFCl_3$
$^c$electron ionization and/or chemical ionization with $CH_4$

EXAMPLE 5

In a typical reaction, 100 g of 1,1-di(orthoxylyl) methane is heated to its boiling point in a vaporizer while purging with nitrogen gas. The 1,1-di(orthoxylyl) methane/nitrogen gas stream is fed to a heated reactor 6" diameter and 4' long containing approximately 35 lbs of cobalt trifluoride. The reactor is held at approximately 345° C. in the first half of the reactor and approximately 415° C. in the last half of the reactor. The 1,1-di(orthoxylyl) methane feed converts to approximately 200 g of a perfluorochemical. The crude fluorochemical can be filtered to remove any solids and can be passed through alumina to remove any active fluorides.

EXAMPLE 6

2602 g of a perfluorochemical prepared in a similar manner as shown in Examples 2 and 3 were distilled in a high efficiency packed column. A product was collected which had a boiling range of 250°–260° C. This fraction represented 40% of the original fluorochemical charge. The boiling point was determined to be 255° C. Analysis by $^{19}F$ NMR spectroscopy and GC/MS (gas chromatography/mass spectroscopy) confirmed the presence of perfluoro-1,1-di(orthoxylyl) methane as reported in Table 2 below and the presence of perfluoro-1,1-di(orthoxylyl) ethane as reported in Table 3 below.

TABLE 2

| $^a$NMR-$^{19}$F | | |
| --- | --- | --- |
| $CF_3$ $-63$ to $-73^b$ multiplet | $CF_2$ $-98$ to $-140^b$ multiplet | $CF$ $-161$ to $-189^b$ multiplet |
| Relative F atomic ratio | | |
| calculated 2.0 | 2.3 | 1.0 |
| observed 1.6 | 1.9 | 1.0 |
| $^c$MASS SPECTRUM (m/e) | | |
| calculated | | 812 ($C_{17}F_{32}$) |
| observed | | 812 ($C_{17}F_{32}$) |

$^a$in $CFCl_3$
$^b$ppm from $CFCl_3$
$^c$electron ionization and/or chemical ionization with $CH_4$

TABLE 3

| $^a$NMR-$^{19}$F | | |
| --- | --- | --- |
| $CF_3$ $-63$ to $-80^b$ multiplet | $CF_2$ $-98$ to $-140^b$ multiplet | $CF$ $-161$ to $-180^b$ multiplet |
| Relative F atomic ratio | | |
| calculated 2.0 | 1.7 | 1.0 |
| observed 1.8 | 1.9 | 1.0 |
| $^c$MASS SPECTRUM (M/E) | | |
| calculated | | 862 ($C_{18}F_{34}$) |
| observed | | 862 ($C_{18}F_{34}$) |

$^a$in $CFCl_3$
$^b$ppm from $CFCl_3$
$^c$electron ionization and/or chemical ionization with $CH_4$

EXAMPLE 7

In a typical reaction, 100 g of 1,1-di(orthoxylyl) propane is heated to its boiling point in a vaporizer while purging with nitrogen gas. The 1,1-di(orthoxylyl) propane/nitrogen gas stream is fed to a heated reactor 6" in diameter and 4' long containing approximately 35 lbs of cobalt trifluoride. The reactor is held at approximately 345° C. in the first half of the reactor and approximately 415° C. in the last half of the reactor. The 1,1-di(orthoxylyl) propane feed converts to approximately 200 g of a perfluorochemical containing perfluoro-1,1-di(orthoxylyl) propane. The crude fluorochemical can be filtered to remove any solids and can be passed through alumina to remove any active fluorides.

The compounds can also be synthesized by other fluorination techniques, including direct fluorination with elemental fluorine under mild conditions, as well as fluorination using other fluorine sources than cobalt trifluoride. As stated previously, the compounds display unique stability and appropriate high temperature boiling point to make them useful for vapor phase soldering, particularly of solder fluxes that melt slightly below the boiling point of the compounds.

In vapor phase soldering, a component is typically affixed to a pretreated substrate. Such component or article can constitute a miniaturized electronic component such as an integrated circuit or transistor, or the like, wherein the article is assembled to a substrate, such as a printed circuit board or hybrid circuit board, with a solder preform or is adhered to such substrate with a solder paste while the paste is still in a tacky state. After the preform and article are assembled, or the article is adhered and the paste is dry, the assembly is then placed in the vapor zone of a container of the boiling vapor phase soldering working fluid; perfluoro-1,1-di(orthoxylyl) methane, ethane, propane or mixtures thereof. The vapor of the compound as it boils is heavier than air and therefore will tend to remain in a settled condition over the bath of boiling liquid. The vapor will maintain the temperature of the boiling point of the liquid and upon immersion of the article, component or assembly into the vapor zone, the vapor will condense on the relatively cooler article, assembly or component and thereby impart the heat of vaporization of the condensing vapor on the article, assembly or component. The heat of the vapor, being limited to the boiling point of the liquid compound, will control the maximum heat that the article, assembly component is subjected to, and this heat is designed to be approximately 30° C. above the melting point of the solder preform or solder paste. The effect is that the solder is melted and appropriately solders the joint of the article, assembly or component, while avoiding any detrimental high heat effects to the other portions of the article, assembly or component. The soldered article, assembly or component is then removed from the fluid vapor and cooled under preferably ambient conditions, or alternately, a second fluid medium which is below the melting point of the solder is utilized to perform such cooling function.

Alternatively, the same working fluid comprising perfluoro-1,1-di(orthoxylyl) methane, ethane, propane or mixtures thereof can be utilized in wave soldering wherein the article or component does not utilize a solder preform or solder paste, but rather is assembled by pins into a substrate such as a circuit board wherein the article or component is immersed in the vapor of the working fluid sufficient to heat the article to near solder reflow conditions. Then the heated article is contacted with a solder wave so as to coat the appropriate portions of the assembly, article or component so as to solder contacts or pins of the article or component to, potentially, a substrate such as a circuit pattern of printed circuit board.

Integrated soldering of surface mounted components and through-hole components in a simultaneous reflow and solder spray technique, can also be performed in the vapor of perfluoro-1,1-di(orthoxylyl) methane, ethane, propane or mixtures thereof. In such a technique, some components on a board are soldered by the heat of the condensing vapor compound, thereby reflowing solder preforms or solder paste, while other through-hole components are soldered by the application of molten solder to the underside of the circuit board. The solder application can be from a wave or a spray of solder. The solder in the application technique can be heated by a source other than the perfluoro-1,1-di(orthoxylyl) methane, ethane, propane or mixtures thereof.

The technique for soldering, fusing or brazing with a working fluid constituting perfluoro-1,1-di(orthoxylyl) methane, ethane, propane or mixtures thereof wherein the vapor phase of the working fluid condenses on the article or component in order to transfer the heat of vaporization to the article or component for the purposes of soldering, fusing or brazing provides an attractive and advantageous method for performing these operations, such as was not available to the prior art. The preferred mode of operation constitutes the condensation soldering or wave soldering of components using such a compound as the heat transfer media and these techniques may be utilized in either a batch or continuous mode. The compound provides an unexpectedly good match of the characteristics which are known to be required of a working fluid for operation in this field. Specifically, the compound has a boiling point at least equal to or preferably above the melting point of tin-silver solders presently widely utilized in the electronic component industry for assembly of certain electronic components. When in the pure form of the desired perfluoro-1,1-di(orthoxylyl) methane, ethane or propane, the working fluid should have a well defined boiling point, which provides better temperature control over the process. It is preferred to operate the process with highly pure perfluoro-1,1-di(orthoxylyl) methane, ethane or propane so as to effectively have a single component working fluid. However, it is understood that nondetrimental amounts of isomers and impurities may be incorporated into the compound working fluid without departing from the invention. The perfluoro-1,1-di(orthoxylyl) methane, with a boiling point of 250° C., is preferable to the industry standard FC-71 for the tin-silver solders having a compositional range of approximately 96.5% tin to 3.5% silver which are necessary for high demand, high tech. electronic and for initial soldering of multisided circuit boards. In addition, as the temperature of the soldering operation increases, the criticality of stability, inertness and avoidance of toxic by-product formation such as perfluoroisobutylene formation, is very important. The perfluoro-1,1-di(orthoxylyl) methane, ethane and propane will exhibit such enhanced stability at such higher temperatures as well as being liquid at room temperature which is a surprising improvement over the hydrocarbon precursors and very important for soldering utilities.

The perfluoro-1,1-di(orthoxylyl) methane has utility as a high temperature vapor phase soldering fluid as exemplified in the following example.

EXAMPLE 8

A vapor phase soldering apparatus was charged with a liquid containing 70% perfluoro-1,1-di(orthoxylyl) methane and 30% perfluoro-1,1-di(orthoxylyl) ethane and allowed to reflux. A solder paste consisting of 96.5% tin and 3.5% silver was used to coat a printed circuit board. A surface mounted device was positioned on the solder paste and the entire assembly was immersed in the perfluoro-1,1-di(orthoxylyl) methane/ethane reflux zone. Solder reflow was observed to occur in approximately 30 seconds. Upon removal of the circuit assembly, no fluorochemical residue was observed, but clean substantial reflow of the solder was observed and the assembly comprising the surface mounted device and printed circuit board were firmly affixed by the operation of the solder.

Fluorinated amine compounds, such as perfluoro trihexylamine, have been known to produce even minor amounts of perfluoroisobutylene which is highly toxic. Perfluoro-1,1-di(orthoxylyl) methane and ethane have been subjected to testing under cyclic high temperature operation, in the presence of metals, solders and other materials which may constitute inadvertent catalyst systems for the material if used in vapor phase soldering applications, to identify the quantity of perfluorosobutylene by-product of the compound of the invention. Results of tests sampling the vapor and effluent of heated perfluoro-1,1-di(orthoxylyl) methane and ethane have shown negligible or nondetectible perfluoroisobutylene by-product levels when tested with gas chromatograph equipment.

The perfluoro-1,1-di(orthoxylyl) methane, ethane or propane compounds also have utility as an oxygen transport media for invivo and invitro applications in their form as pure substances or in mixture or emulsion form, as well as utility as a hydraulic fluid, a lubricant and other applications where chemical inertness and boiling point are the desired physical and chemical properties. Finally the unexpected attribute of their liquid state at room temperatures makes them highly desireable for vapor phase soldering wherein retention on soldered components is to be avoided and salting out or residue formation is detrimental.

The scope of the present invention should be ascertained from the claims which follow:

We claim:

1. The composition having the structural formula:

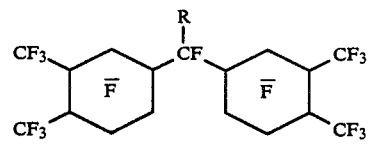

wherein $\bar{F}$ indicates that all available sites are fluorinated and there are no carbon to carbon double bonds and R is selected from the group consisting of F, $CF_3$ and $C_2F_5$.

2. The composition of claim 1 wherein R is F.
3. The composition of claim 1 wherein R is $CF_3$.
4. The composition of claim 1 wherein R is $C_2F_5$.

* * * * *